United States Patent
Sato et al.

(10) Patent No.: US 7,135,331 B2
(45) Date of Patent: *Nov. 14, 2006

(54) APPARATUS FOR DETECTING BIOPOLYMERS AND CARTRIDGE

(75) Inventors: Keiichi Sato, Kanagawa (JP); Mitsuhiro Tachibana, Kanagawa (JP); Toshiki Morita, Kanagawa (JP); Motonao Nakao, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 15 days.

This patent is subject to a terminal disclaimer.

(21) Appl. No.: 11/048,918

(22) Filed: Feb. 3, 2005

(65) Prior Publication Data

US 2005/0136470 A1 Jun. 23, 2005

Related U.S. Application Data

(62) Division of application No. 10/001,012, filed on Nov. 30, 2001, now Pat. No. 6,875,603.

(30) Foreign Application Priority Data

Nov. 30, 2000 (JP) .............................. 2000-364370

(51) Int. Cl.
*C12M 1/34* (2006.01)
(52) U.S. Cl. .............................. 435/288.1; 435/285.2; 435/287.2; 204/194; 204/400; 204/403.01; 356/246; 359/398
(58) Field of Classification Search ...................... None
See application file for complete search history.

(56) References Cited

U.S. PATENT DOCUMENTS

| | | | |
|---|---|---|---|
| 3,579,433 A | 5/1971 | Dahlgren | |
| 4,552,640 A | 11/1985 | Kartenbeck | |
| 5,059,294 A | 10/1991 | Lizardi | |
| 5,151,165 A | 9/1992 | Huynh | |
| 5,246,866 A | 9/1993 | Nasu et al. | |
| 5,307,148 A | 4/1994 | Kambara et al. | |
| 5,314,602 A | 5/1994 | Kambara et al. | |
| 5,472,881 A | 12/1995 | Beebe et al. | |
| 5,942,397 A | 8/1999 | Tarlov et al. | |
| 6,013,166 A | 1/2000 | Heller | |
| 6,107,080 A * | 8/2000 | Lennox | 204/403.01 |

(Continued)

FOREIGN PATENT DOCUMENTS

DE 3110804 3/1981

(Continued)

OTHER PUBLICATIONS

Office Action from Japanese Patent Office dated May 10, 2005 in Japanese.

*Primary Examiner*—David Redding
(74) *Attorney, Agent, or Firm*—Reed Smith LLP; Stanley P. Fisher, Esq.; Juan Carlos A. Marquez, Esq.

(57) ABSTRACT

Provided is an apparatus for detecting biopolymers (DNA) capable of total analysis including non-reacted samples without complicated operations such as washing.

A DNA probe is fixed to one of electrodes and direct current voltage is placed between the electrodes, so that it becomes possible to separate complementary strand sample DNA and non-complementary strand sample DNA. By analyzing from a ratio in the whole reaction system, it is possible to obtain clearer results. Further, by using electrophoresis by gel together, it is possible to separate reacted samples and non-reacted samples to perform measurements therefor in the same reaction field.

7 Claims, 8 Drawing Sheets

U.S. PATENT DOCUMENTS

| | | |
|---|---|---|
| 6,129,828 A | 10/2000 | Sheldon, III et al. |
| 6,315,940 B1 * | 11/2001 | Nisch et al. ............. 435/287.1 |
| 6,582,954 B1 | 6/2003 | Sato et al. |

FOREIGN PATENT DOCUMENTS

| | | | |
|---|---|---|---|
| EP | 0 366 408 A2 | | 10/1989 |
| EP | 0 457 526 A2 | | 5/1991 |
| JP | 6098799 | | 8/1993 |
| JP | 6098799 | * | 4/1994 |
| JP | 2000-60554 | | 8/1998 |
| JP | 2000/279169 | | 6/1999 |
| WO | WO 98.58251 | | 5/1998 |
| WO | WO99/64581 | * | 12/1999 |

\* cited by examiner

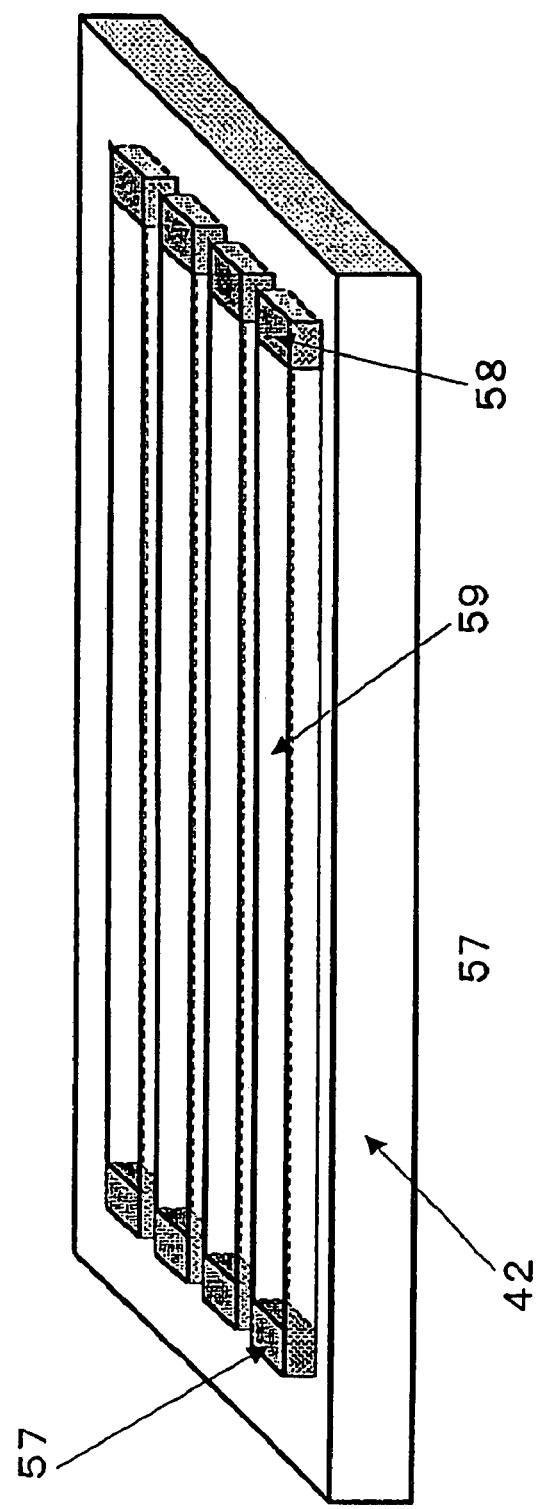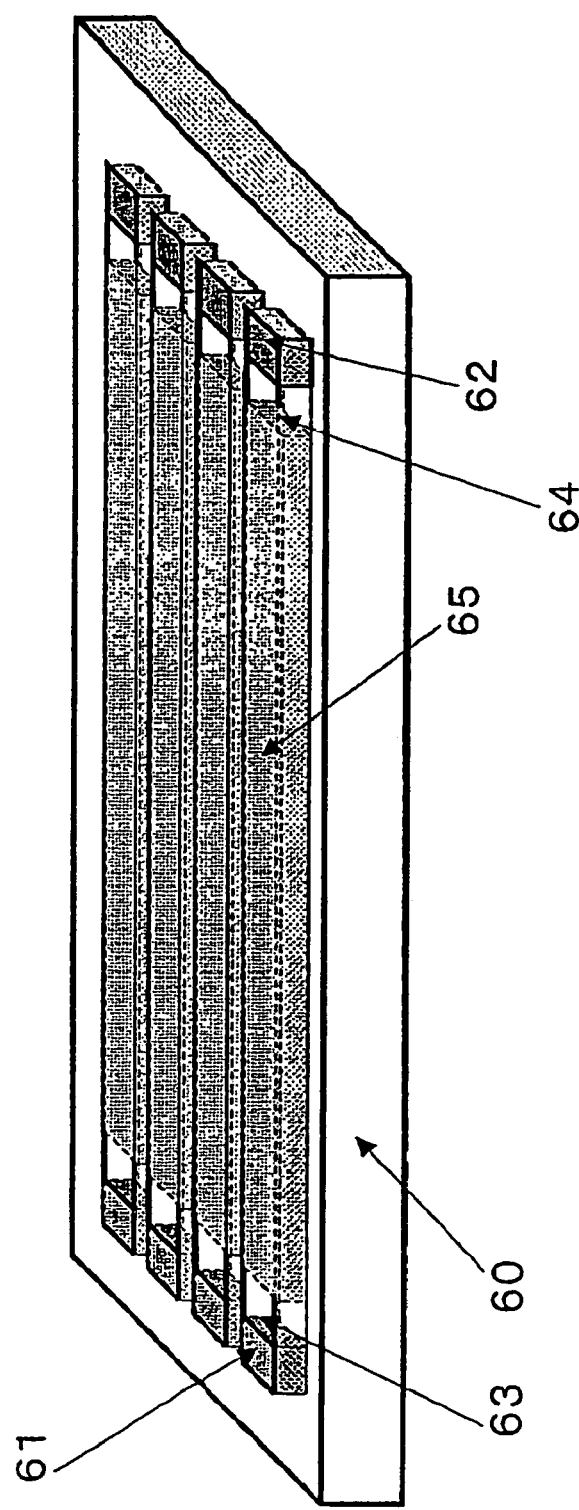
FIG.5A
FIG.5B electric field

APPARATUS FOR DETECTING BIOPOLYMERS AND CARTRIDGE

CROSS-REFERENCE TO RELATED APPLICATION

This application is a Divisional of U.S. Ser. No. 10/001,012 filed Nov. 30, 2001 now U.S. Pat. No. 6,875,603. Priority is claimed based on U.S. Ser. No. 10/001,012 filed Nov. 30, 2001, which claims priority to Japanese Patent Application No. 2000-364370 filed on Nov. 30, 2000.

PRIORITY INFORMATION

This application claims priority to Japanese Application Serial No. 364370/2000, filed Nov. 30, 2000.

BACKGROUND OF THE INVENTION

The present invention relates to an apparatus for detecting biopolymers capable of detecting the presence of biopolymers such as DNA, RNA and protein in a sample and measuring an existing amount or a concentration thereof, and to a cartridge used for the detection.

As technologies for detecting DNA, such technology has been generally used, in which DNA is modified with a radioactive material, a fluorescence dyestuff or the like by use of technologies of RI (radioactive isotope), fluorescence or the like and excited by a stimulus from the outside for detection of response by luminescence. Also an electric charge detecting method for electrochemically determining DNA based on an oxidation-reduction potential by use of an intercalating agent, which is specifically bonded to a duplex of DNA, has been devised. Further, there is a method of using a surface plasmon resonance phenomenon as a method without modification and the like. With respect to a method of fixing DNA to an electrode, there is a method of utilizing an action that a monolayer of free thiol radicals located on the end of DNA is self-organized on the surface of gold using a thiol modified DNA probe.

In conventional DNA detecting technologies, methods of using RI or fluorescence have been needed to modify DNA.

SUMMARY OF THE INVENTION

An apparatus for detecting biopolymers in accordance with the present invention includes: a voltage supply unit for placing electric voltage between two electrodes of a cartridge which stores biopolymers between the electrodes; a holding unit for holding the cartridge; an irradiation unit for irradiating light onto the cartridge held by the holding unit; and a light receiving unit for receiving the light irradiated by the irradiation unit onto the cartridge held by the holding unit.

The voltage supply unit can selectively supply alternating current voltage and direct current voltage so that biopolymers can be attracted to one electrode or both electrodes.

The holding unit can two-dimensionally move the cartridge on a plane perpendicular to an optical axis of the light irradiated by the irradiation unit so that the presence of a biopolymer on each location in the cartridge can be detected.

Since the irradiation unit can irradiate light having a specified single wavelength, sensitivity for detecting can be improved.

The apparatus for detecting biopolymers further includes an arithmetic unit for calculating an existing amount, a base length, a concentration, a hybridization ratio and a hybridization amount of a biopolymer from a quantity of light received by the light receiving unit so that various kinds of feature amounts for the biopolymer can be determined.

The apparatus for detecting biopolymers further includes a heater which applies heat to the electrodes of the cartridge for disassociating biopolymers hybridized in the cartridge to single strands, so that each presence of a complementary strand biopolymer and a non-complementary strand biopolymer can be detected.

Also, a cartridge in accordance with the present invention includes: a pillar-shape base unit capable of accommodating a biopolymer solution, the base unit having a first electrode on the inside of a bottom face, transparent sides at least in a portion and a top face opened; and a cap unit which has a second electrode on the outside of a bottom face and is inserted in the base unit from the top face to the middle of the base unit to be fixed.

Since biopolymer probes are fixed on the first electrode or the second electrode, a complementary strand biopolyiner and a non-complementary strand biopolymer can be separately detected.

Further, the cross section of the pillar-shape base unit is a square and the cross section of the cap unit is a round shape. Therefore, since a light incident plane is a plane surface, it is possible to suppress light scattering and easily insert the cap unit into the base unit.

Also, the cartridge further includes a solution reservoir on an upper portion of the base unit for collecting a biopolymer solution overflowed from said pillar-shape portion to prevent the solution from flowing out so that it is possible to prevent the solution from flowing out to the outside.

In the apparatus for detecting of the present invention, a sample DNA is injected between electrodes facing each other. In this technology, since an existing amount of DNA can be physically measured, a concentration thereof and the like can be also determined. Further, by applying an external force by an electric field between the facing electrodes to attract single strand probe DNA fixed on the surface of the electrode and non-hybridized sample DNA to the electrode where the probe DNA is not fixed, it becomes possible to detect a gene without washing.

Further, by use of this method, clearer results can be obtained since both of reacted one and non-reacted one are targeted for the measurement.

DESCRIPTION OF THE DRAWINGS

FIGS. 5A and 5B are views showing a plate-shape cartridge in detail.

DETAILED DESCRIPTION

Hereunder, referring to drawings, preferred embodiments will be described in details.

Figure 1:
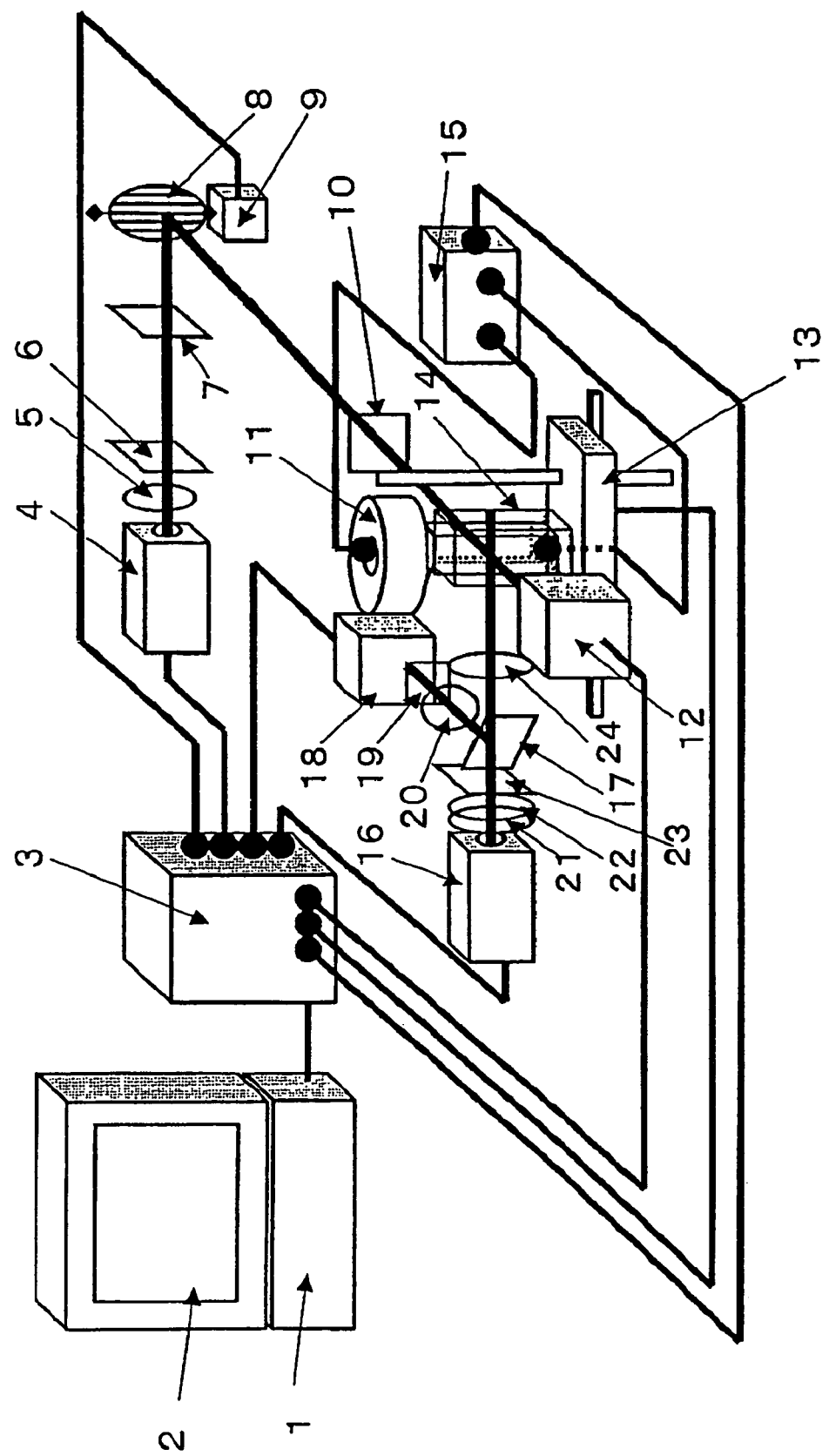
FIG. 1 is a schematic view showing a structure of an apparatus for detecting biopolymers according to one embodiment in the present invention.

FIG. 1 is a schematic view showing a structure of an apparatus for detecting biopolymers according to one embodiment of the present invention. The apparatus includes an optical system to measure optical energy and the like, such as absorbance, transmittance and reflectance, and an optical system to detect a modified part when DNA is modified with an organic material or an inorganic material, such as a fluorescent material and a radio active material.

Figure 2:
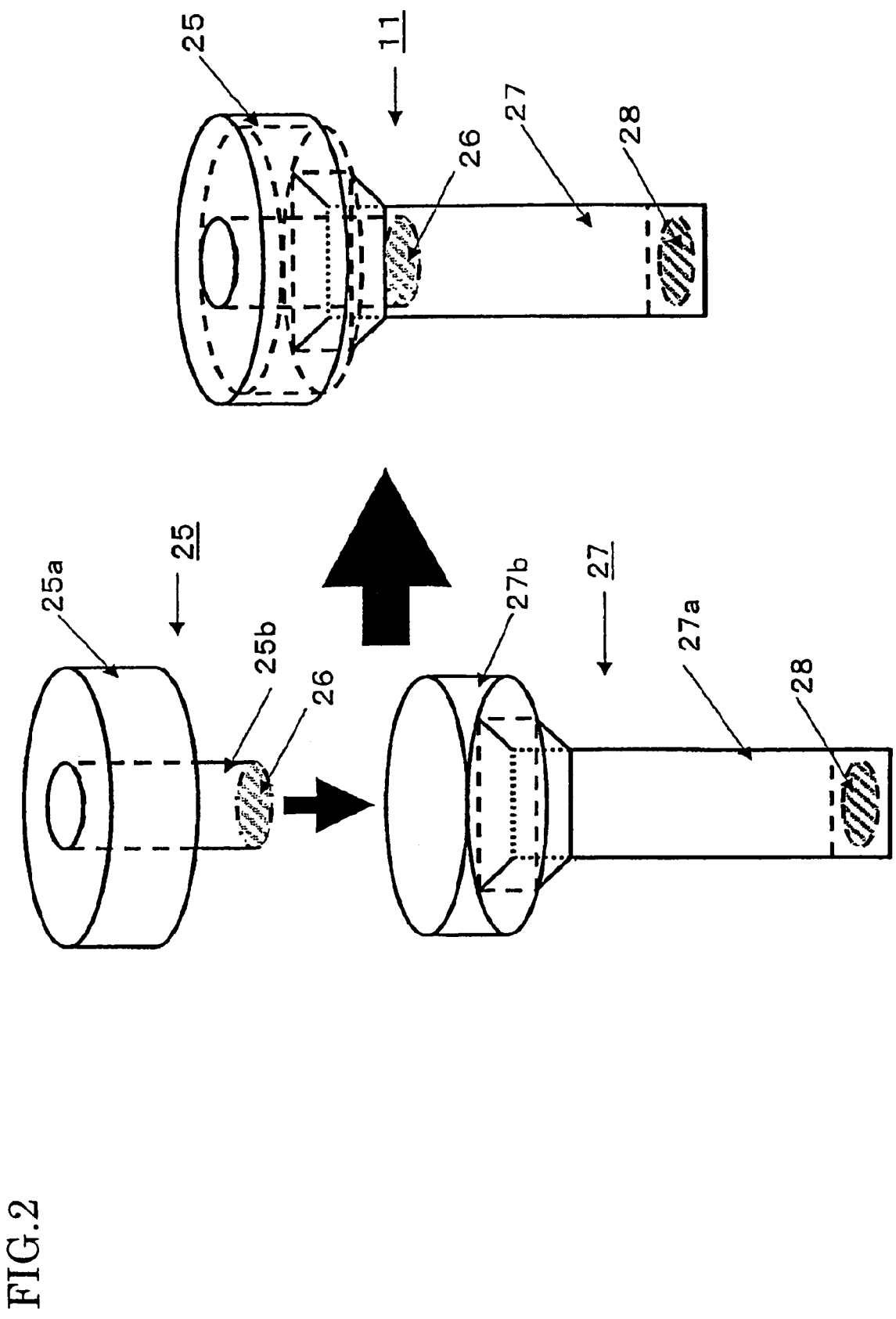
FIG. 2 is a view showing a structure of a cartridge according to one embodiment in the present invention.

The optical system to measure optical energy and the like, such as absorbance, transmittance and reflectance, includes a laser, an optical source, a slit, a filter, a diffraction grating, a light receiving unit and the like. A controller 3 is connected to a computer 1 having a display 2. Light generated from a laser and optical source 4 controlled with the controller 3 is passed through an optical source slit 6 after wavelength selection with a filter 5. The light is passed through an incidence slit 7 and converted to have wavelengths of 260 nm and 280 nm at a diffraction grating 8. Further, the light is passed through an ejection filter 10 placed just before a cartridge 11, the details of which are shown in FIG. 2). Optical energy is decreased in the cartridge 11 depending on an existing amount of DNA since DNA absorbs the light. That is, optical energy after the decrease is obtained at a light receiving unit 12. Any desired measurement location can be selected using an XY stage 13, and reading can be conducted in a scanning manner. Analysis of the result is carried out with the computer 1, and a distribution of the DNA existing amount can be determined by measuring how much the quantity of optical energy received at the light receiving unit is decreased from incident light at some place. The transmittance is obtained as a ratio of a quantity of light to that in the case of no presence of DNA under the condition that the cartridge 11 is fully filled with the solution. The reflectance is, in the same manner, obtained as a ratio of a quantity of reflected light to that in the case of no presence of DNA. In order to measure this reflectance, an optical system to receive the reflected light is needed. The absorbance is obtained by subtracting transmittance from reflectance. Temperature inside the cartridge can be controlled by a cartridge fixed portion 14 provided with an electric heater that is connected to a power source 15. Thus, the temperature during reaction or measurement can be controlled, and the reactivity at each temperature, such as a dissociation temperature for single strands, for example, can be measured.

The optical system to detect a modified part when DNA is modified with an organic material or an inorganic material, such as a fluorescent material or a radio active material, includes a laser, a light source, a pinhole, a lens and the like. Light generated from a laser and light source 16 is condensed with a lens 22 after passing through a filter 21 for wavelength selection and is passed through a pinhole 23 at the focal point. The light passed through the pinhole 23 is again condensed with the lens 24 having the focal point at a measuring portion. The light indicating a material excited by the condensed light is advanced to the lens 24 and is advanced through a polarized beam splitter 17 to a light receiving unit 18 side. The light having a selected wavelength by passing through a filter is passed through a pinhole 19 at the focal point to reach the light receiving unit 18. A distribution of modified parts is analyzed based on signals from the light receiving unit 18.

FIG. 2 is a view showing a structure of a cartridge according to one embodiment of the present invention. A cartridge 11 includes a cap unit and a base unit 27. In the cap unit 25, at a top face thereof, an inner cylinder 25b having a bottom face opened and a smaller cross section is coaxially joined to an outside pillar 25a having a bigger cross section. An electrode 26 is provided on the outside of the whole bottom face of the inner cylinder 25b. The base unit 27 has a round shape electrode 28 on the inside of the bottom face of a hollow square pillar 27a having a square cross section. A top face of the square pillar 27a is opened so that a DNA solution is injected and the cap unit 25 can be inserted. Further, a solution reservoir 27b is provided on an upper portion of the square pillar 27a to prevent the DNA solution from flowing out to the outside when some of the DNA solution overflows from the square pillar 27a. With respect to the cartridge 11, there are ones where DNA probes are fixed to both electrodes, DNA probes are fixed to one of the electrodes and DNA probes are fixed to neither electrode. The cartridge 11 is inserted into a cartridge insertion portion of the apparatus. The apparatus has electrodes to generate an electric field in the cartridge 11 so that direct current voltage and/or alternating current voltage supplied from a power source can be placed between the electrodes in the cartridge 11.

Detection is carried out by measuring optical energy such as absorbance, transmittance and reflectance of light having a wavelength of 260 nm. The measurement is carried out by comparison in a plurality of ranges or scanning in a tiny range. Based on a distribution of the obtained optical energy such as absorbance, transmittance and reflectance, a distribution of DNA existing between the electrodes can be obtained to determine an existing amount, a concentration, a hybridization ratio, a hybridization efficiency of DNA and the like.

Figure 7:
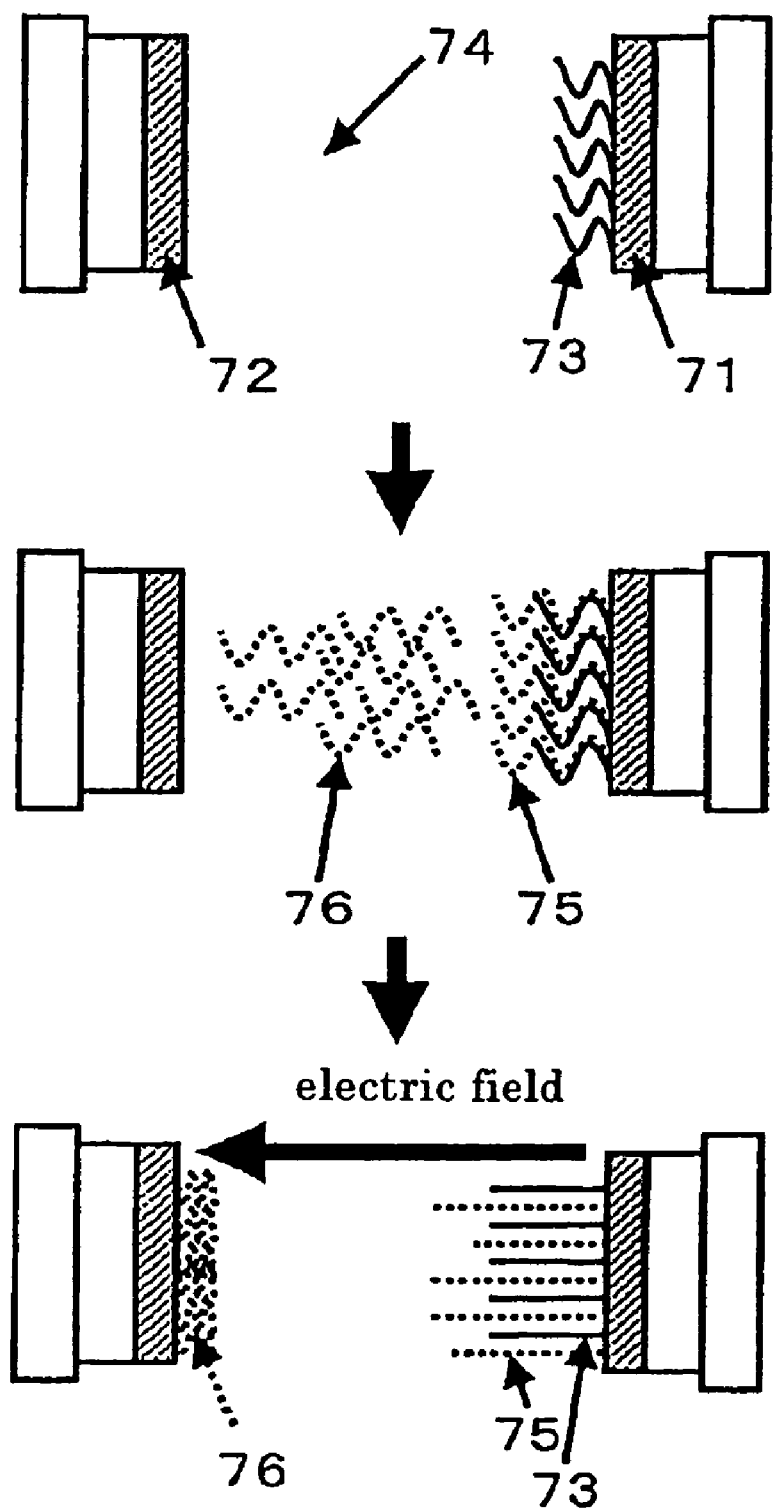
FIG. 7 is a view showing behaviors of DNA when direct current voltage is applied.

FIG. 7 is a view showing DNA behaviors when direct current voltage is applied. When direct current voltage is applied between an electrode 71 and an electrode 72, DNA is drawn in a direction of the electric field and attracted to one of the electrodes, electrode 72 in this case. For this reason, when probe DNA 73 is fixed on the electrode 71 and direct current voltage applied between the electrodes after hybridization reaction, complementary strand sample DNA 75, which was hybridized, is fixed to the electrode 71 to be prolonged, but non-complementary strand sample DNA 76, which was not hybridized, is attracted to the electrode 72 side to be a shrunk state. By measuring the DNA amount at each location in this state, the amount and the base length of the hybridized complementary strand sample DNA 75 and the amount of the non-complementary strand sample DNA 76, which was not hybridized, can be determined. Specifically, the base length can be determined by measuring where the end of DNA is prolonged and exists.

Figure 8:
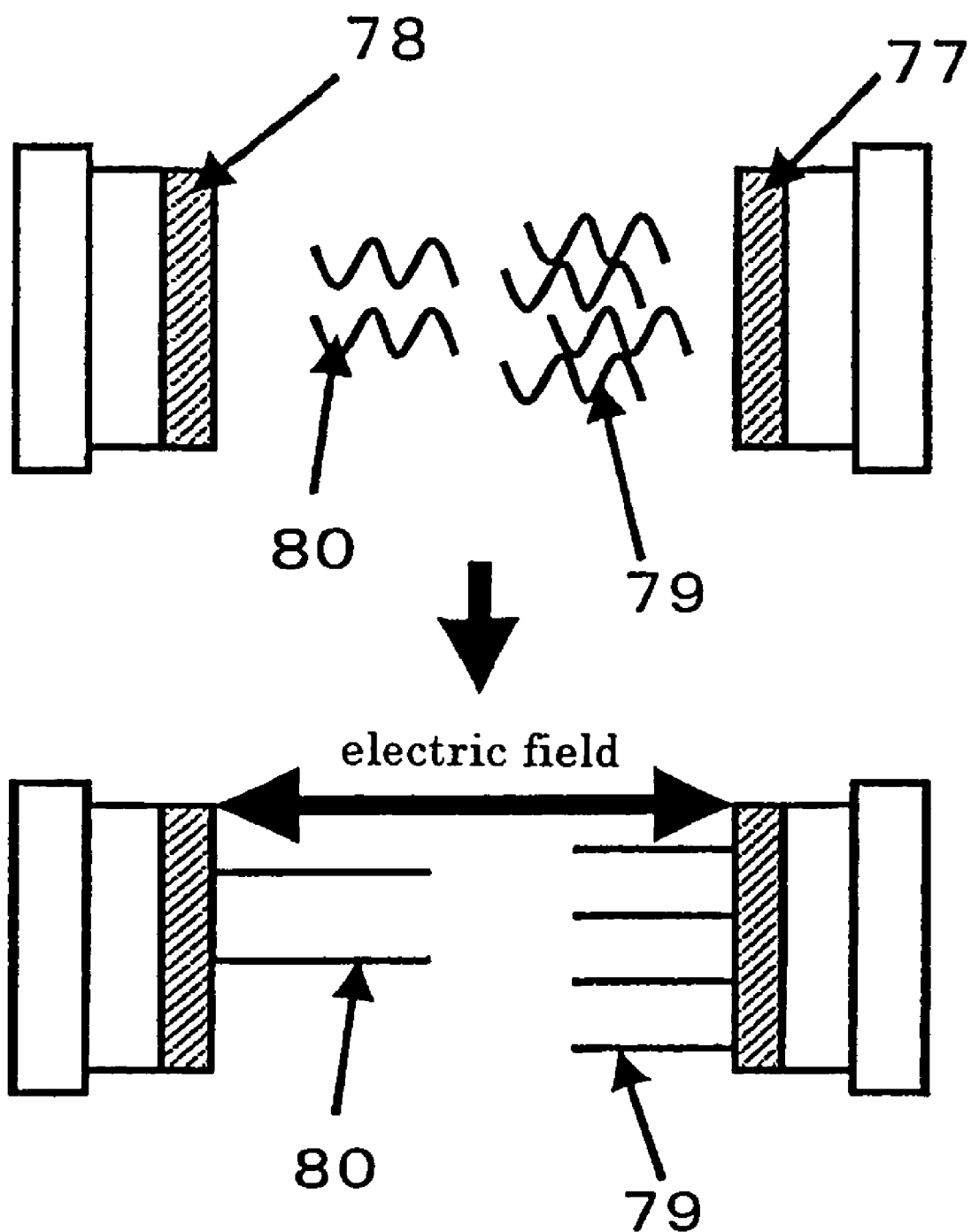
FIG. 8 is a view showing behaviors of DNA when alternating current voltage is applied.

FIG. 8 is a view showing DNA behaviors when alternating current voltage is applied. When alternating current voltage is applied between an electrode 77 and an electrode 78, DNA is drawn, in a prolonged state, from the location before the application of voltage to the closer electrode at some range of frequency and voltage, 1 MHz and 106 V/m in the present apparatus. In the present embodiment, a sample DNA 79 existing at a location closer to the electrode 77 becomes elongated at the location closer to the electrode 77. A sample DNA 80 existing at a location closer to the electrode 78 becomes elongated at the location closer to the electrode 78. By separately and repeatedly using direct current voltage and alternating current voltage as voltage applied to the cartridge 11, it is possible to control the location of DNA. In the present apparatus, direct current voltage is applied between the electrodes at each of the stage of attracting DNA between electrodes at the time of injection of a sample, the stage of attracting sample DNA to the probe side before hybridization reaction and the stage of separating sample DNA forming a duplex with the probes and non-reacted sample DNA after hybridization reaction. Alternating current voltage is applied when DNA is stretched in a separated state at the time of measuring the base length and the like.

Figure 3:
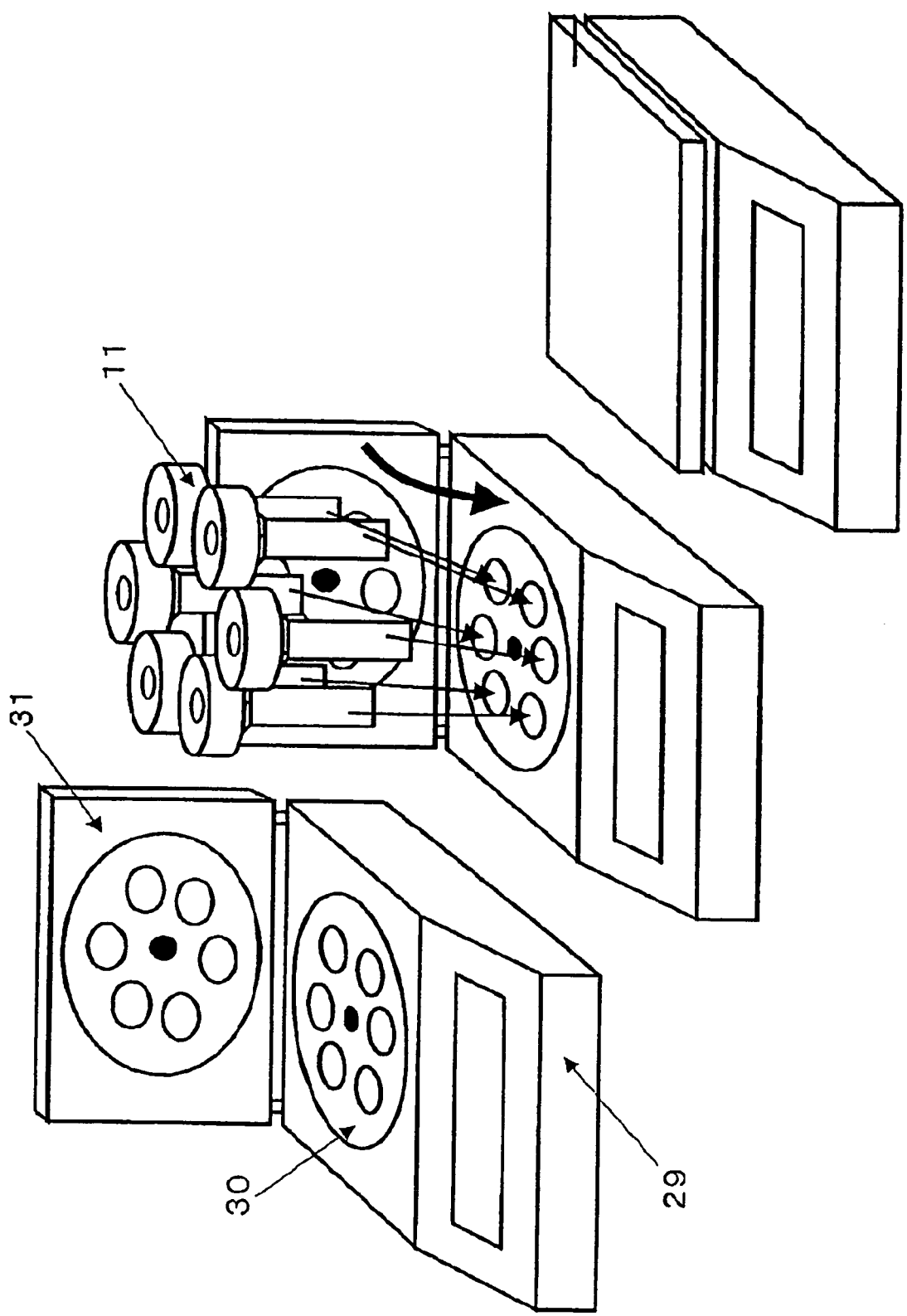
FIG. 3 is a general view showing an apparatus for detecting biopolymers according to one embodiment in the present invention.

FIG. 3 is a general view of the apparatus for detecting biopolymers according to one embodiment of the present invention. A rotary cartridge inserting part 30 is provided in the main unit 29 of the apparatus. The plurality of cartridges 11 are loaded thereon, and a cover unit 31 of the apparatus is closed. Therefore, DNA detection can be continuously conducted by automatically changing the cartridges 11 to be subjected to the measurement.

Figure 4:
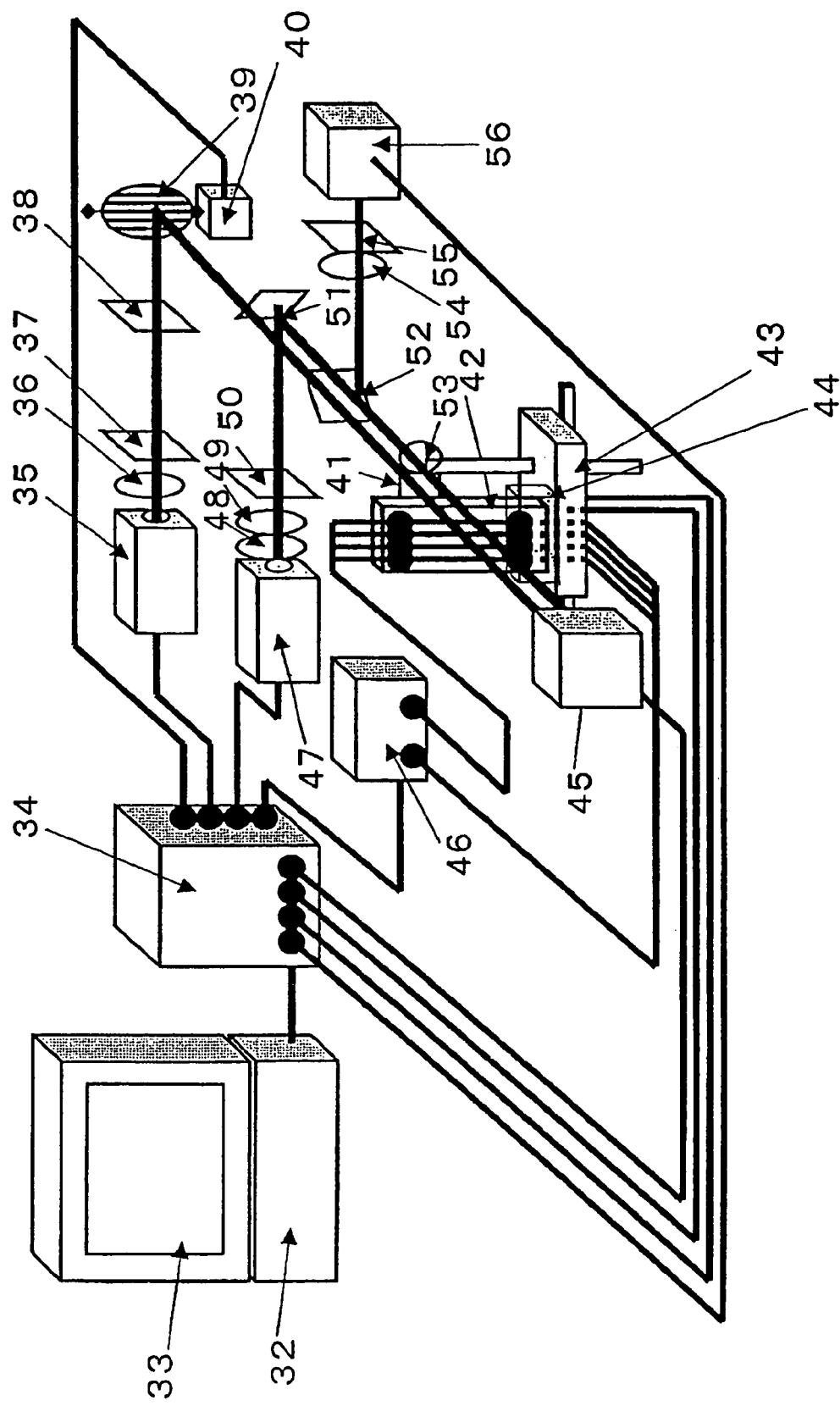
FIG. 4 is a schematic view showing a structure of an apparatus for detecting biopolymers using plate-shape cartridges.

FIG. 4 is a schematic view showing a structure of the apparatus for detecting biopolymers using a plate-shape cartridge, the details of which is shown in FIG. 5. An optical system to measure optical energy and the like, such as absorbance, transmittance and reflectance, includes a laser and a light source, a slit, a filter, a diffraction grating, a light receiving unit and the like. Light generated from a laser and light source 35, after wavelength selection with a filter 36, is passed through a light source slit 37. The light is passed through an incident slit 38 and converted to have wavelengths of 260 nm and 280 nm with a diffraction grating 39. Further, the light is passed through an ejection slit 41 placed just before the cartridge. Optical energy is decreased in a plate-shape cartridge 42 depending on an existing amount of DNA since DNA absorbs the light. That is, optical energy after the decrease is obtained at a light receiving unit 45. Any desired measurement location can be selected using an XY stage 43, and reading can be conducted in a scanning manner. Analysis of the result is carried out with a computer 32, and a distribution of the DNA existing amount can be determined by measuring how much the quantity of optical energy received at the light receiving unit 45 is decreased from incident light at some place.

An optical system to detect a modified part when DNA is modified with an organic material or an inorganic material, such as a fluorescent material or a radio active material, includes a laser and a light source, a pinhole, a lens and the like. Light generated from a laser and light source 47 is condensed with a lens 49 after passing through a filter 48 for wavelength selection and is passed through a pinhole 50 at the focal point. The light is turned to the plate-shape cartridge 42 with a reflecting mirror 51 and is again condensed with the lens 53 having the focal point at a measuring portion. The light indicating a material excited by the condensed light is advanced to the lens 53 and is advanced through a polarized beam splitter 52 to a light receiving unit 56. The light having a selected wavelength by passing through a filter 54 is passed through a pinhole 55 at the focal point to reach the light receiving unit 56. Analysis of the distribution of modified parts is conducted with a computer 32 based on signals from the light receiving unit 56. Temperature inside the cartridge can be controlled by a cartridge fixed portion 44 provided with an electric heater that is connected to a power source 46. Thus, the temperature during reaction or measurement can be controlled, and the reactivity at each temperature, such as a dissociation temperature for single strands, for example, can be measured.

FIGS. 5A and 5B are views showing a plate-shape cartridge in details. A plate-shape cartridge shown in FIG. 5A has a structure, in which storing ditches 59 having micro widths and depths are provided on a plate, and electrodes 57 and 58 are provided on the both sides of each of the storing ditches 59. When the absorbance, the transmittance and the like are measured, a transparent bottom face is needed. As for the measurement, optical energy such as absorbance, transmittance and reflectance and the like is measured. The conventional detection by fluorescence can be carried out.

FIG. 5B is a view showing plate-shape cartridges having gel. By putting gel 65 in the middle of the storing ditches and heating electrodes 61 and 62, it is possible to conduct a time lag measurement. Single-strand DNA probes are fixed to one electrode 61 beforehand and a sample DNA solution is injected in each of wells 63 located on the side of the electrode 61, to which the probes are fixed, for hybridization reaction. Measurement is performed for non-reacted sample DNA by conventional electrophoresis. When DNA and modified materials in gel portion 65 have completely flowed out into the well 64 located on the side of the electrode 62 facing the electrode 61, the electrode 61 is heated to dissociate DNA existing around the electrode 61 to single strands, and the measurement is again performed by conventional electrophoresis. By this way, it is possible to determine a base length distribution and an existing amount of complementary strand DNA and a base length distribution and an existing amount of non-complementary strand DNA in the sample DNA.

In the measurement and the detection, it is possible to use unmodified sample DNA, but it is possible to obtain higher sensitivity by modifying DNA with an organic material or an inorganic material, such as a fluorescent dyestuff, for excitation from an outside stimulus.

Figure 6:
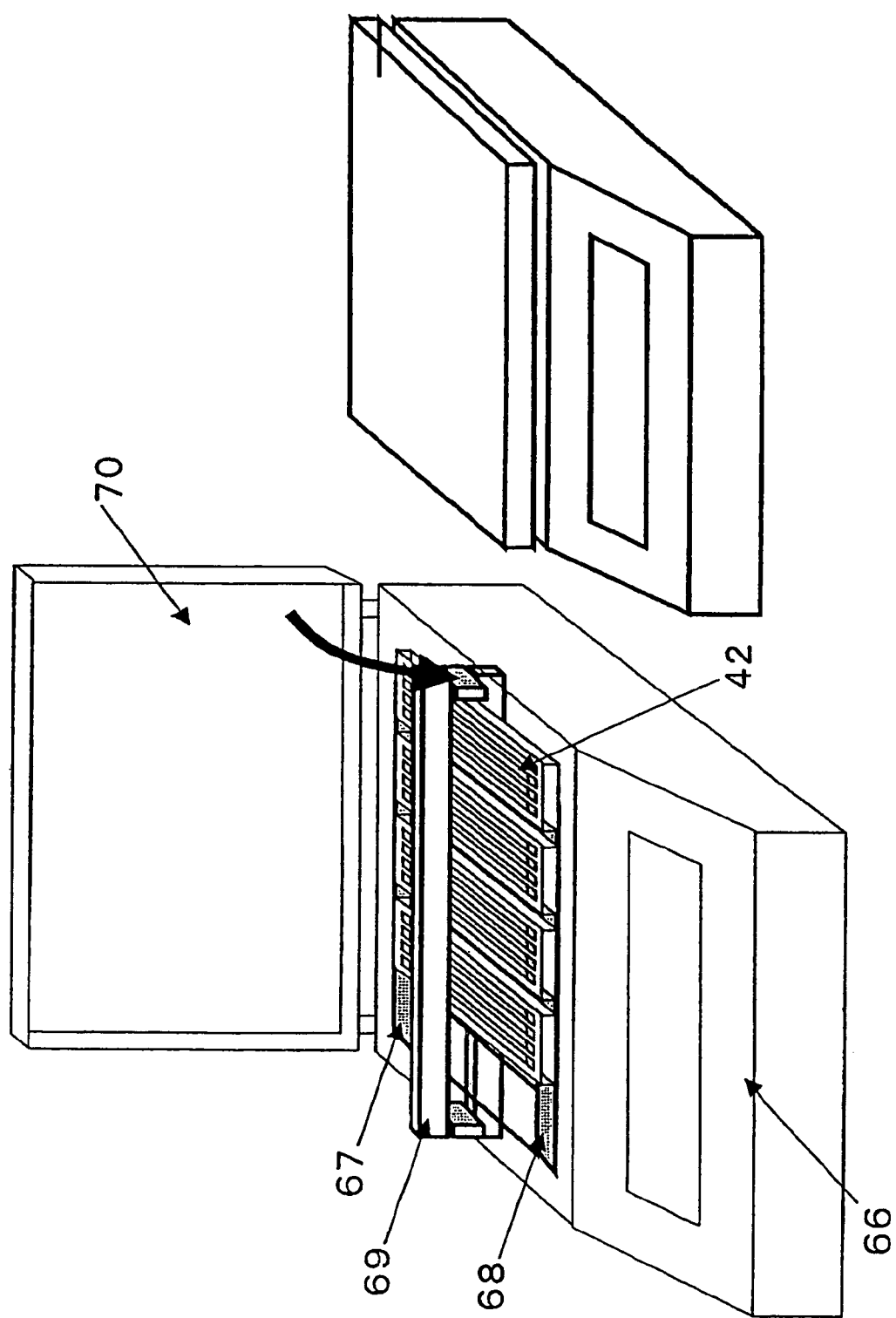
FIG. 6 is a general view showing an apparatus for detecting biopolymers using the plate-shape cartridges.

FIG. 6 is a general view of the apparatus of detecting biopolymers having plate-shape cartridges. A plurality of plate-shape cartridges 42 are loaded in a main unit 66 of the apparatus so that the electrodes of the cartridge are connected to be in contact with one electrode 67 and the other electrode 68. The cartridges are scanned in one time with a scanning part 69. Usually, hybridization or electrophoresis is conducted while a lid 70 is closed.

Note that the present invention is not limited to the embodiment mentioned above.

In the embodiment mentioned above, the cross section of the cartridge is a square, but other shapes such as a hexagon may be acceptable. It is desirable that the cartridge has transparent and parallel planes in order to avoid scattering of light passing therethrough.

Moreover, dissociation temperature for single strands of DNA can be determined by varying temperature of the electrodes and by measuring an amount of hybridized DNA or non-hybridized DNA at each temperature.

In accordance with the present invention, the presence and an existing amount or a concentration of a biopolymer such as DNA, RNA and protein and the like in a sample can be simply determined.

What is claimed is:

1. A cartridge comprising:
  a pillar-shape base unit capable of accommodating a biopolymer solution, the base unit having a first electrode on the inside of a bottom face, transparent sides at least in some portion and a top face opened; and a cap unit which has a second electrode on the outside of a bottom face and is inserted to be fixed in said base unit from the top face to the middle of the base unit.

2. The cartridge according to claim 1, wherein a biopolymer probe is fixed on the first electrode or the second electrode.

3. The cartridge according to claim 1, wherein a cross section of said pillar-shape base unit is a square and a cross section of said cap unit is a round shape.

4. The cartridge according to claim 1, wherein a biopolymer probe is fixed on one of the first electrode and the second electrode, and a cross section of said pillar-shape base unit is a square and a cross section of said cap unit is a round shape.

5. The cartridge according to claims 1, further comprising a solution reservoir on an upper portion of said base unit for collecting a biopolymer solution overflowed from said pillar-shape portion to prevent the solution from flowing out to the outside.

6. The cartridge according to claim 1, wherein a biopolymer probe is fixed on one of the first electrode and the second electrode, and further comprising a solution reservoir on an upper portion of said base unit for collecting a biopolymer solution overflowed from said pillar-shape portion to prevent the solution from flowing out to the outside.

7. The cartridge according to claim 1, wherein a cross section of said pillar-shape base unit is a square and a cross section of said cap unit is a round shape, and further comprising a solution reservoir on an upper portion of said base unit for collecting a biopolymer solution overflowed from said pillar-shape portion to prevent the solution from flowing out to the outside.

* * * * *